US006528063B2

United States Patent
Stram et al.

(10) Patent No.: US 6,528,063 B2
(45) Date of Patent: *Mar. 4, 2003

(54) RECOMBINANT VACCINES AGAINST IBDV

(75) Inventors: Yehuda Stram; Arie Rogel; Ilan Sela; Orit Edelbaum; Yehoshua Shachar; Yehuda Zanberg; Tanya Gontmakher; Eli Khayat, all of Western Galilee (IL)

(73) Assignees: Rahan Meristem, Rosh Hanikra (IL); Shafit, Shefaim (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/477,574

(22) Filed: Jan. 4, 2000

(65) Prior Publication Data

US 2002/0015708 A1 Feb. 7, 2002

Related U.S. Application Data

(60) Provisional application No. 60/114,634, filed on Jan. 4, 1999.

(51) Int. Cl.[7] .................. A61K 39/12; A61K 48/00; C12N 15/33; C12N 5/14; A01H 5/00
(52) U.S. Cl. .................. 424/204.1; 424/93.21; 435/69.3; 435/419; 800/298; 800/317.2; 800/317.3
(58) Field of Search .................. 424/204.1, 93.21; 435/69.3, 419; 800/298, 317.2, 317.3

(56) References Cited

FOREIGN PATENT DOCUMENTS

WO          96/40229    * 12/1996   .......... A61K/39/00

OTHER PUBLICATIONS van Bokhoven et al. Journal of general virology, Nov. 1990, 71: 2509–17 (abstract only).*
Modelska et al. PNAS 95:2481–2485, Mar. 1998.*
Carillo et al. Journal of Virology 72(2):1668–1690, Feb. 1998.*
Dalsgaard et al. Nature Biotechnology 15(3):248–52, abstract only cited, 1997.*
Vakharia et al. Journal of General Virology 74:1201–1206, 1994.*
Hoshi et al. Vaccine 13(3):245–252, 1995.*

* cited by examiner

Primary Examiner—Mary E. Mosher
(74) Attorney, Agent, or Firm—Kohn & Associates, PLLC

(57) ABSTRACT

There is provided a stable vaccine for providing protection against disease having viral proteins transgenically expressed in plant cells. Also provided is a stable vaccine which provides protection against disease containing viral protein and coding sequences cloned into an *E. coli* expression system. A method of vaccination by transgenically expressing viral proteins capable of providing protection against disease into plant cells and administering the plant cells to an animal in need of vaccination is also provided. Also provided is a method of vaccination by cloning viral protein and coding sequences capable of providing protection against disease into an *E. coli* expression system and administering the *E. coli* into the animal in need of vaccination.

11 Claims, 11 Drawing Sheets

Figure 2
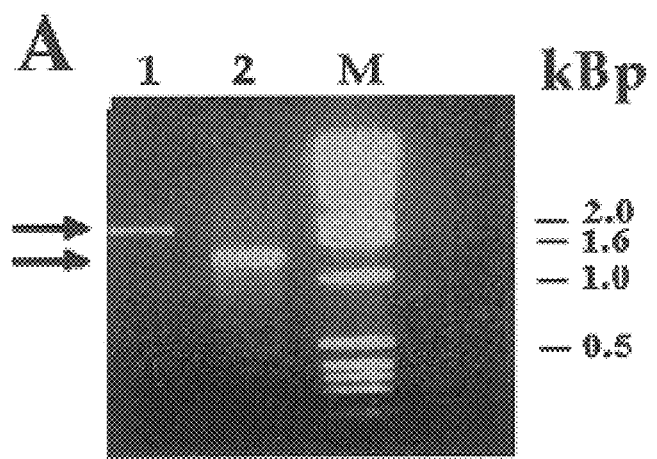
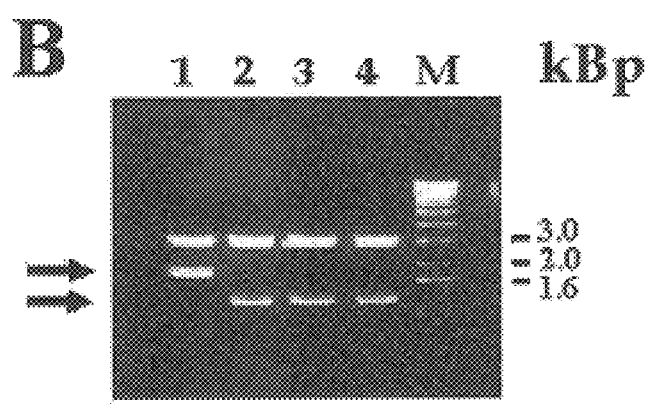
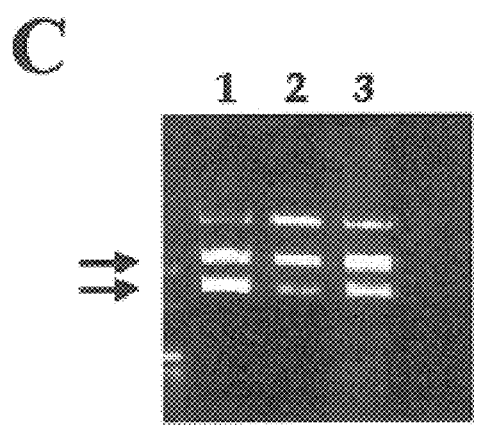

Figure 3
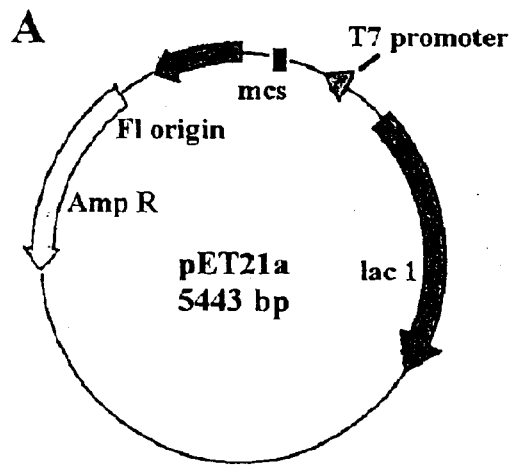
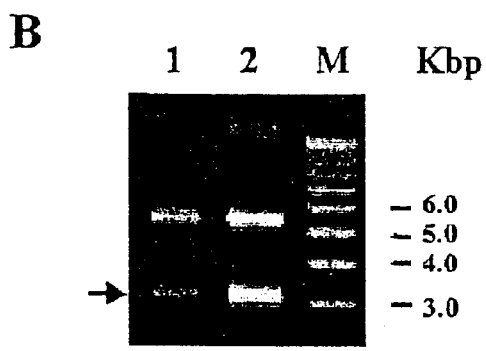
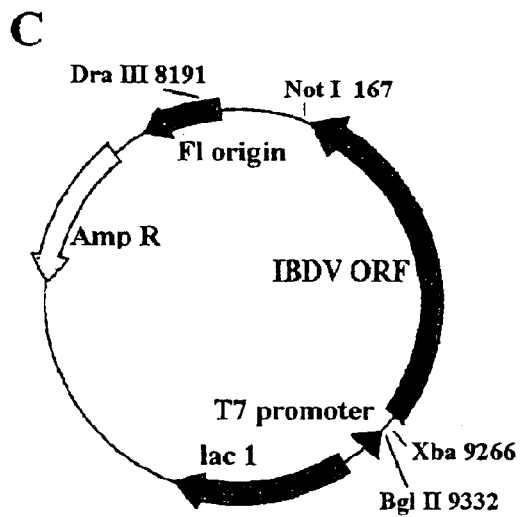

Figure 4

LOCUS       nkit434063  3054 bp  RNA          VRL     05-NOV-2001
DEFINITION  Genome A polyprotein translation region.
ACCESSION   bankit434063
SOURCE      Gumboro virus.
ORGANISM    Infectious bursal disease virus  Viruses; dsRNA viruses;
Birnaviridae; Avibirnavirus.
REFERENCE   1  (bases 1 to 3054)
AUTHORS     Stram,Y., Rogel,A., Sela,I., Edelbaum,O., Shachar,Y.,
Zanberg,Y., Gontmakher,T. and Khayat,E.
TITLE       Vaccination of Chickens against Infectious Bursal Disease Virus
(IBDV) by Empty Particles expressed in E.coli
JOURNAL     Unpublished
REFERENCE   2  (bases 1 to 3054)
AUTHORS     Stram,Y., Rogel,A., Sela,I., Edelbaum,O., Shachar,Y.,
Zanberg,Y., Gontmakher,T. and Khayat,E.
TITLE       Direct Submission
JOURNAL     Submitted (05-NOV-2001) Virology, Kimron Veterinary
Institute, P.O.Box 12, Beit Dagan 50250, Israel
COMMENT     Bankit Comment: CDS 16..3048 viral protein precursor.
FEATURES            Location/Qualifiers
     source        1..3054
                   /organism="Infectious bursal disease virus"
                   /db_xref="taxon:10995"
                   /note="ds RNA viruses; Birnaviridea; Gumboro virus;
                   Israeli gep 5 isolate;"
BASE COUNT      823 a    855 c    792 g    584 t
ORIGIN
        1 caaacgatcg cacatatgac aaacctgcaa gatcaaaccc aacagattgt tccgttcata
       61 cggagccttc tgatgccaac aaccggaccg gcgtccattc cggacgacac cctagagaag
      121 cacactctca ggtcagagac ctcgacctac aatttgactg tggggggacac agggtcaggg
      181 ctaattgtct ttttccctgg tttctctggc tcaattgtgg gtgctcacta cacactgcag
      241 agcaatggga actacaagtt cgatcagatg ctcctgactg cccagaacct accggccagc
      301 tacaactact gcaggatagt gagtcggagt ctcacagtga ggtcaagcac actccctggc
      361 ggcgtttatg cactaaatgg caccataaac gccgtgttcc aaggaagcct gagtgaactg
      421 acagatgtta gctacaatgg gttgatgtct gcaacagcca acatcaacga caaaatcggg
      481 aacgtcctag taggggaagg ggtaaccgtc ctcagcttac ccacatcata tgatcttggg
      541 tatgtgagac tcggtgaccc catcccgct ataggctcg acccaaaaat ggtagcaaca
      601 tgtgacagca gtgacaggcc cagagtctac accataactg cagccgatga ttaccaattc
      661 tcatcacagt accaagcagg tggagtaaca atcacactgt tctcagctaa tatcgatgcc
      721 atcacaagcc tcagcatcgg ggaagaactc gtgtttcaaa caagcgtcca aggccttata
      781 ctgggcgcta ccatctacct tataggcttt gatgggactg cggtaatcac cagagctgtg
      841 gccgcagaca atgggctaac ggccggcact gacaacctta tgccattcaa tattgagatt
      901 ccaaccagcg agataaccca gccaatcaca tccatcaaac tggagatagt gacctccaaa
      961 agtggtggcc aggcgggggga tcagatgtca tggtcagcaa gtgggagcct
agcagtgacg

Figure 4 cont.

```
1021 atccacggtg gcaactatcc aggggccctc cgtcccgtca cactagtagc ctacgaaaga
1081 gtggcaacag gatctgtcgt tacggtcgcc ggggtgagca acttcgagct gatcccaaat
1141 cctgaactag caaagaacct ggtcacagaa tacggccgat ttgacccagg
ggccatgaac
1201 tacacaaaat tgatactgag tgagagggac cgtcttggca tcaagaccgt gtggccaaca
1261 agggagtaca ctgactttcg cgagtacttc atggaggtgg ccgacctcaa ctctcccctg
1321 aagattgcag gagcatttgg cttcaaagac ataatccggg ccctaaggag gatagctgtg
1381 ccggtggtct ctacactgct cccacccgcc gctcccctag cccatgcaat tggggaaggt
1441 gtagactacc tgctgggcga tgaggcacaa gctgcttcag gaactgctcg agccgcgtca
1501 ggaaaagcaa gagctgcctc aggccgcata aggcagctaa ctctcgccgc
cgacaagggg
1561 tacgaggtag tcgcgaatct gtttcaggtg ccccagaatc ctgtagtcga cgggattctc
1621 gcttcacctg gggtactccg cggtgcacac aacctcgact gcgtgttgag agagggtgcc
1681 acgctatttc ctgtggtcat cacgacagtg gaagatgcca tgacacccaa agcgctgaac
1741 agcaaaatgt ttgctgtcat tgaaggcgtg cgagaagatc tccaacctcc atctcaaaga
1801 ggatccttca tacgaactct ctccggacat agagtctatg gatatgctcc agatggggta
1861 cttccactgg agactgggag agattacacc gtggtcccaa tagatgatgt ctgggacgac
1921 agcattatgc tgtccaatga ccccatacct cctattgtgg gaaacagcgg aaacctagcc
1981 atagcttaca tggatgtgtt tcgacccaaa gtccccatcc atgtggccat gacgggagcc
2041 ctcaacgcct atggcgagat tgagaacgtg agctttagaa gcaccaagct cgccactgca
2101 caccgacttg gcctcaagtt ggctggtccc ggtgcatttg acgtgaacac cgggtccaac
2161 tgggcgacgt ttatcaaacg ttttcctcac aatccacgcg actgggacag gctcccttac
2221 ctcaaccttc catacccttcc acccaatgca ggacgccagt acgacctggc catggccgct
2281 tcagagttca aagagacccc cgaactcgag agcgccgtca gagccatgga
agcagcagcc
2341 aacgtggacc cactgttcca atctgcgctc agcgtgttca tgcggctgga agagaatggg
2401 attgtgactg atatggccaa cttcgcactc agcgacccga acgcccatcg gatgcgcaat
2461 tttctcgcaa acgcaccaca agcaggcagc aagtcgcaaa gagccaagta
cgggacagca
2521 ggctacggat tggaagcccg gggcccccact ccagaggaag cacagaggaa
aaaagacaca
2581 cggatatcaa agaagatgga gactgtgggc atctactttg caacaccaga atgggtagca
2641 ctcaatgggc accgggggcc aagccccggc cagctaaagt actggcagaa
cacacgagaa
2701 atacctgatc caaacgagga ctacctagac tacgtgcatg cagagaagag ccggttggca
2761 tcagaagaac aaatcctaag ggcagctacg tcgatctacg gggctccagg
acaggcagag
2821 ccaccccagg ccgtcataga cgaagtcgcc aaagtctatg aaatcaacca
tgggcgtggc
2881 cccaaccaag aacagatgaa agatctgctc ttgactgcga tggagatgaa gcatcgcaat
2941 cccaggcggg ctccaccaaa gcccaagcca aaacccaatg ttccaacaca
gagaccccct
3001 ggtcggctgg gccgctggat cagggctgtc tctgacgagg accttgagta aggc
//
```

Figure 6

Recombinant IBDV particles in *E. coli* cells

Immuno-blot analysis of IBDV protein expression

Figure 9

LB – Left border
RB – Right border
RSSU – Rubisco small subunit promoter
NPTII – Neomycin phosphor-transferase gene
CaMV35S – Cauliflower mosaic virus 35S promoter

RECOMBINANT VACCINES AGAINST IBDV

CROSS REFERENCE TO RELATED APPLICATIONS

This application is a conversion of U.S. Provisional Patent Application Ser. No. 60/114,634, filed Jan. 4, 1999, incorporated herein by reference.

TECHNICAL FIELD

The present invention relates to poultry vaccinations. More specifically, the present invention relates to vaccines against infectious bursal disease virus (IBDV).

BACKGROUND OF THE INVENTION

Vaccines which stimulate the mucosal immune system can be used to immunize, generally via an oral route, hosts against pathogens that are transmitted via the gastrointestinal, respiratory and urogenital tracts. These vaccines stimulate the mucosal immune system. See for example Shalaby, "Development of oral: vaccines to stimulate mucosal and systemic immunity: barriers and novel strategies" *Clin Immunol Immunopathol* 74(2):127-134, 1995; Mestecky et al, "Mucosal immunity and strategies for novel microbial vaccines" Acto Paediatr Jpn, 36(5):53744, 1994; U.S. Pat. Nos. 5,518,725 and 5,417,986.

The mucosal immune system operates through the mucosa-related IgA and a complement of T cells with mucosa-specific regulatory or effector properties and provides for host defense at the mucosal surfaces. For a more complete review of the mucosal immune system see Strober and James, "The Mucosal Immune System" In *Basic & Clinical Immunology 8th Edition* eds Stites, Terr, Parslow, (Appleton & Lange, 1994), pgs 541–551, incorporated by reference in its entirety.

Infectious Bursal Disease (IBD) is a widespread disease in poultry. It is caused by a virus, which belongs to a recognized family Birnaviridae. IBD virus attacks the young bird's immune system and causes severe illness, usually around 4–6 weeks of age. Symptoms include depression, diarrhea, muscular hemorrhage, necrosis of the bursa and sever damage to the immune system. Mortality of infected birds is high and survivors exhibit slow growth and high susceptibility to other infectious diseases. Several vaccines are available and others have been attempted as detailed in the prior art. The costs of these vaccines make it impractical to use them, particularly in developing parts of the world. In addition, several of the vaccines require sophisticated storage and administration, which again possesses problems for use in many parts of the world. Another problem with the conventional vaccines (attenuated or killed viruses) is the possibility of reconstitution of virulence of the immunizing agents. It is therefore an object of this invention to produce safe and inexpensive vaccine, which can be produced in cells of *E. coli* and administered by injection or orally.

Infectious Bursal Disease (IBV) is widespread and caused by IBD Virus (IBDV). Chickens with the virus present with symptoms of diarrhea, muscular hemorrhage, necrosis of the bursa of Fabricius and severe immune system damage. Mortality is high and surviving chickens exhibit growth retardation and disease susceptibility. There are several vaccines available and other have been attempted.

However, as set forth previously, the costs of these vaccines make it impractical to use them, particularly in developing parts of the world. In addition several of the vaccines require sophisticated storage and administration which again poses problems for use in many parts of the world.

It is therefore an object of this invention to produce a vaccine which stimulates the mucosal immune system and which can be administered orally and which is inexpensive and easy to use.

SUMMARY OF THE INVENTION

According to the present: invention, there is provided a stable vaccine for providing protection against disease having viral proteins transgenically expressed in plant cells. Also provided is a stable vaccine which provides protection against disease containing viral protein and coding sequences cloned into an *E. coli* expression system. A method of vaccination by transgenically expressing viral proteins capable of providing protection against disease into plant cells and administering the plant cells to an animal in need of vaccination is also provided. Also provided is a method of vaccination by cloning viral protein and coding sequences capable of providing protection against disease into an *E. coli* expression system and administering the *E. coli* into the animal in need of vaccination.

BRIEF DESCRIPTION OF THE DRAWINGS

FIGS. 2 A–C are photographs depicting agarose gel electrophoresis of amplified cDNA fragments stained with ethidium bromide and viewed over a UV lamp;

FIGS. 3 A–C are schematic representations of the vector pET21a and pKVI206 (FIGS. 3A and C respectively) and 3B is a photograph showing the agarose gel electrophoresis of amplified cDNA fragments stained with ethidium bromide and viewed over a UV lamp; Lane 1 shows the Xba I/NotI digest of pKVI206; lane 2 shows to Xba I/NotI digest of pKVI207;

FIG. 4 is the nucleotide sequence of the amplified IBDV cDNA fragment in pKV1206 (SEQ ID No:1).

FIG. 6 is a photograph showing the scanning electron microscope (SEM) microscopy of IPTG induced *E. coli* cells (pKVI206-BL21) harboring empty IBDV particles (indicated by arrows);

FIG. 8 is a photograph showing the Western blot analysis of anti-IBDV antibodies in the serum of vaccinated chickens with purified recombinant empty IBDV particles;

FIG. 9 is a schematic representation of the structure of the binary plasmid pBi203.

DETAILED DESCRIPTION OF THE INVENTION

Figure 1:
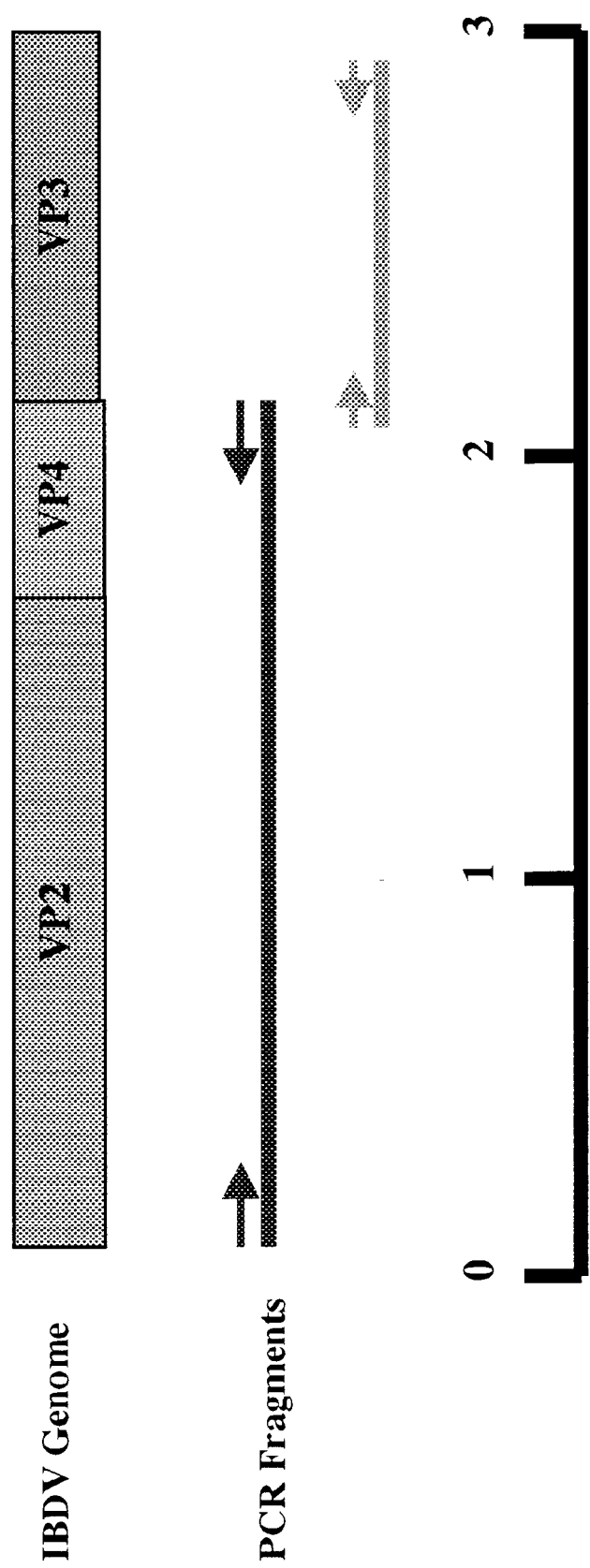
FIG. 1 is a schematic representation of the PCR strategy for amplifying the entire IBDV A genome, the size of the fragment is scaled in the bottom line.

Generally, the present invention provides a vaccine for protection against disease, the vaccine contains viral proteins either transgenically expressed in plant cells or cloned into an *E. coli* expression system. Also provided by the present invention is a method of vaccinating animals by either transgenically expressing the viral proteins capable of providing protection against disease into plant cells or cloning viral protein encoding sequences capable of providing protection against disease into an *E. coli* expression system and then administering either the plant cells or *E. coli* to an animal in need of the vaccination.

The present vaccine was developed against IBDV for immunization by expressing the two viral structural proteins either in *E. coli* expression vector or in plant cells. By way of background, the IBDV virion consists of two proteins VP2 and VP3. The viral genome consists of two dsRNA the largest genome fragment A encodes for three proteins, the two structural proteins VP2, VP3 and the viral protease VP4. Fragment B encodes for the viral polymerase. The larger fragment (A) 3.2 kbp fragment which contains three VP2-4 genes in one open reading frame. Translation of this genome in the infected cells produce one long polyprotein that is cleaved by viral VP4 protease to get the mature VP2 and VP3.

Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., Current Protocols in Molecular Biology, John Wiley and Sons, Baltimore, Md. (1989). Additionally, standard methods in immunology known in the art and not specifically described are generally followed as in Stites et al. (eds), *Basic and Clinical Immunology* ($8^{th}$ Edition), Appleton & Lange, Norwalk, Conn. (1994) and Mishell and Shiigi (eds), *Selected Methods in Cellular Immunology*, W. H. Freeman and Co., New York (1980).

Delivery systems (vectors) for delivering the expression cassette to the target cell are known in the art and a nonexhaustive list is provided herein below. Of particular interest are viral vectors as discussed. below. Alternatively, a cell based system is used as a method of site-specific delivery (targeting) to the tumorogenic cells. the cells are generally selected from cells that shed and/or release the expression cassette to be incorporated by the tumorogenic cells as is known in the art. These cell are selected from cells that will "home" to the site of the tumorogenic cells. Alternatively, other methods know in the art for site specific delivery of cells are used to deliver the cells in situ.

Vectors which comprise the DNA encoding for a clone of the expression library are also provided by the present invention. The vectors can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

In order to create the vaccine, the viral proteins were transfected/cloned into either a plant cell or an *E. coli* expression vector. Referring more specifically to the use of plant cells for providing the vaccination, by feeding the animals with the transgenic plants expressing the assembled viral proteins, this will provide the mucosal immune system that will induce immunity against the virus infection. Any plant cell can be utilized which is able to be ingested by the animal which is fed the transgenic plant cells. In the preferred embodiment, tobacco or potato plants are used because in these plants the expression; is constitutive. By constitutive, it is meant that all of the organs of the plants. express the antigens.

The entire expressed. assembled viral protein is tranfected/cloned into either the plant cell or *E. coli* expression vector because, it has been established previously that in many cases immunization with only one recombinant viral protein, even with the most immunogenic one, does not necessarily induce the necessary protection state. However, immunization can be guaranteed with a fully assembled virion.

In order to produce these plant cells which express the assembled viral proteins, transgenic plants must be created containing therein the assembled viral proteins. The process of creating these transgenic plants is set forth in the $15^{th}$ Chapter of *Genetic Engineering of Plants*, incorporated herein by reference.

Some examples of applicable methods include, but are not limited to, growing whole plants from single cells. In this method, single cells (usually from a callus) are removed from a plant and plated out. The cellulose wall of the plant cells can be removed at this time, thus making the protoplast capable of taking up DNA. The cells are then given sufficient nutrients and plant hormones, auxins and cytokinins, for successful regeneration of an entire plant as is commonly known by one of skill in the art. The resulting plant therefore contains therein the desired DNA.

Another example of an applicable method, is the leaf disk technique. This simple technique involves making small leaf disks by punching holes into a leaf. These holes are then inoculated with a plasmid carried by a bacterium, for example Ti plasmid carried by the bacterium *Agrobacterium tumefaciens*. As the, cells at the edge of the disk begin to regenerate, if the cells were sufficiently exposed to the transfecting agent, the transfected cells are selected for by culturing in a suitable medium with an appropriate antibiotic which kills the bacterium. Again, the resulting plant contains the desired DNA.

Other useful techniques include the use of electric shock and guns for the transfer of DNA into the plant cells. Additionally, there is support for the use of viruses as vectors for introducing DNA into plant cells.

Regarding the use of the *E. coli* vector, the present invention is an empty capsid recombinant vaccine providing protection against IBDV. The viral proteins are expressed in the high expression *E. coil* vector. The invention allows for rapid reduction of new vaccines as new strains develop. Further, this can be utilized to provide immunization for other viral diseases that require immunity, particularly in veterinary applications. Specifically, the present invention is an empty capsid recombinant vaccine providing protection against IBDV. The viral proteins are expressed in a high expression *E. coli* vector. The present invention allows for rapid production of new vaccines as new strains develop. It is inexpensive to produce and store and can only replicate in the non-host vector (*E. coli* cells).

Generally, the method utilized for transfecting the expression vector, preferably *E. coli*, first requires primers to be designed specifically for the viral proteins to be encoded. These primers are then used in a Large and Accurate RT-PCR (LA-RT-PCR) process for developing the fragments to be cloned into the vector. In order to express the viral protein in the expression vector, an additional fragment is cloned into the genome between the promoter and terminator of the expression vector. This plasmid is then capable for use in transforming additional cells as required for vaccination.

More specifically, the present invention discloses in the Examples the specific primers utilized in transforming the *E. coli* expression vectors. The present invention can also be used to provide vaccines for other viral diseases that require immunity, particularly in veterinary applications using the same general method set forth above.

The above discussion provides a factual basis for the use of viral proteins in creating a vaccine. The methods used with and the utility of the present invention can be shown by the following non-limiting examples and accompanying figures.

EXAMPLES

GENERAL METHODS

General methods in molecular biology: Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) was carried out generally as in *PCR Protocols: A Guide To Methods And Applications*, Academic Press, San Diego, Calif. (1990). Reactions and manipulations involving other nucleic acid techniques, unless stated otherwise, were performed followed as generally described in Sambrook et al., *Molecular Cloning: A Laboratory Manual*, Cold Springs Harbor Laboratory Press, and methods set forth in U.S. Pat. Nos. 4,666,828; 4,683,202; 4,801,531; 5,192,659 and 5,272,057 and incorporated herein by reference. In-situ (In-cell) PCR in combination with Flow Cytometry was used for detection of cells containing specific DNA and mRNA sequences (Testoni et al., 1996, Blood 87:3822).

General methods in immunology: Standard methods in immunology known in the art and not specifically described were generally followed as in Stites et al. (eds), Basic and Clinical Immunology ($8^{th}$ Edition), Appleton & Lange, Norwalk, Conn. (1994) and Mishell and Shiigi (eds), Selected Methods in Cellular Immunology, W. H. Freemen and Co., New York (1980).

Immunoassays: Generally, ELISAs were the preferred immunoassays to assess specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al., *Molecular Cloning: A Laboratory Manual*, Cold Springs Harbor, New York, 1989.

Antibody production: Antibodies may be either monoclonal, polyclonal or recombinant. Conveniently, the antibodies may be prepared against the immunogen or portion thereof for example a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, Antibodies: *A Laboratory Manual*, Cold Spring Harbor Laboratory, Cold Spring Harbor, N.Y., 1988 and Borrebaeck, *Antibody Engineering—A Practical Guide*, W. H. Freeman and Co., 1992. Antibody fragments may also be prepared from the antibodies and include Fab, $F(ab')_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al., 1991; Johnson and Bird, 1991; Mernaugh and Mernaugh, 1995), messenger RNAs from antibody producing B-lymphocytes of animals, or hybridoma are reverse-transcribed to obtain complimentary DNAs (CDNAs). Antibody cDNA, which can be full or partial length, is amplified and cloned into a phage of a plasmid. The cDNA can be a partial length of heavy and light chain cDNA, separated or connected by a linker. The antibody or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone Thorpe, *Immunochemistry in Practice*, Blackwell Scientific Publications, Oxford, 1982). The binding of antibodies to a solid support substrate is also well known in the art. (see for a general discussion Harlow and Lane, *Antibodies: A Laboratory Manual*, Cold Spring Harbor Laboratory Publications, New York, 1988 and Borrebaeck, *Antibody Engineering—A Practical Guide*, W. H. Freeman and Co., 1992.) The detectable moieties contemplated with. the present invention can include, but are not limited to, fluorescent, metallic, enzymatic and radioactive markers such as biotin, gold, ferritin, alkaline phosphatase, a-galactosidase, peroxidase, urease, fluorescein, rhodamine, tritium, $^{14}C$ and iodination.

EXAMPLE 1

Cloning and Expression of Viral Proteins

Cloning and Expression of Infectious Bursal Disease Virus (IBDV)

A vaccine was developed against IBDV for immunization by expressing the two viral structural proteins in *E. coli*. In many cases, immunization with only one recombinant viral protein, even with the most immunogenic, one will not induce protection state. Only immunization with fully assembled virion can induce immunization. Taking those facts in consideration, the entire viral structural protein was expressed to enable virion assembly.

In recent years, data was accumulated indicating that expression of viral structural proteins tends to fold into a structure similar to authentic virions. This process occurs not only in homologous systems but also in recombinant cells. For example viruses can assemble in prokaryotic cells or animal viruses can be assembled in plant cells.

IBDV virion consists of two proteins VP2 and VP3. The viral genome consists of two dsRNA the largest genome fragment A encodes for three proteins, the two structural proteins VP2, VP3 and the viral protease VP4. Fragment B encodes for the viral polymerase. The larger fragment (A) 3.2 kbp fragment which contains three VP2–4 genes in one open reading frame. Translation of this genome in the infected cells produce one long polyprotein that is cleaved by viral VP4 protease to get the mature VP2 and VP3.

To be able to express the structural proteins in a way that they will be assembled in a recombinant virion, the entire coding sequence of fragment A was cloned into pET *E. coli* expression vector.

Cloning and Expression of IBDV Structural Proteins

Two pairs of primers were designed. Primer IBDV #876 from position 15 to position 39 carries a Not I site at the 5' terminus and Nde I site (CATATG) with the first viral ATG. The reverse primer in this pair was IBDV #12 from position 1806 to 1830. The primer carries the unique Bam HI site of fragment A. The other pair is primer IBDV #18 starting from 1807 to 1831 carrying the same (fragment A) unique Bam HI site and the reverse primer IBDV# 3068 from position 3044 to 3068 containing a Not I site at the 5' prime end.

Using Large and Accurate RT-PCR (LA-RT-PCR), the fragments were developed in the lab using AMV reverse transcriptase and ex-Taq polymerase. Two fragments, 1.8 Kbp (15–1830) and 1.2 Kbp (1807–3068), were amplified (FIG. 1, which depicts a schematic representation of the PCR strategy for amplifying the entire IBDV A genome) and cloned into T/A cloning vector pTargeT (Promega,. Madison, WI) to create pIBDV1.2 and pIBDV1.8, taking advantage of the fact that ex-Taq products carries A residues at each 3' ends of the amplified fragments (FIG. 2). Specifically, FIG. 2A shows the amplification and: cloning of the IBDV A genome. The amplification of IBDV genome is shown as follows: Lane 1, the 1.8 kbp of IBDV PCR product; Lane 2, the 1.2 kbp of IBDV PCR product, Lane M. 1 kb ladder. Additionally, in FIG. 2B there is shown the clones of the IBDV fragments after digestion by Not I-Bam HI as follows: Lane 1, pIBDV1.2 containing 1.2 kbp fragment; Lanes 24, Clones pIBDV1.8 carrying the 1.8 kbp fragment. Finally, in FIG. 2C there is depicted the clones, of pKVI201 203 and 204 bearing the 3.1 kbp IBDV fragment after Not I-Bam HI digestion. More specifically, in FIG. 2C the lanes 1–3 have arrows at the left side of each of the figures indicating IBDV cDNA fragments.

Following cloning, the 1.2 kbp fragment was subcloned from pIBDV1.2 by Not I-Bam HI digestion into the same sites of pIBDV1.8 to create the pKVI201 (FIG. 2C). This plasmid carries the complete coding sequences of IBDV fragment A. To ensure accuracy, the entire clone was sequenced and proved to be one uninterrupted large open reading frame (FIG. 3). More specifically, FIG. 3 depicts the cloning of the IBDV A genome into pET21a vector. FIG. 3A'shows a schematic representation of pET21a. FIG. 3B is a photograph of a gel wherein Lanes 1, 2 are the vectors pKVI 206, 207 after Xba I-Not I digestion. Finally, FIG. 3C is a schematic representation of pKVI206 vector.

To express viral protein in *E. coli* cells, a 3.1 kbp Nde I-Not I fragment starting from the first viral ATG was cloned into Nde I-Not I sites in-between the T7 promoter and terminator of pET21a. The newly constructed plashiid pKVI206 was used to transform BL21 cells carrying the T7 polymerase gene under the IPTG induceable lac Z promoter (FIG. 4, a nucleotide sequence of the IBDV CDNA fragment in pKVI206).

Figure 5:
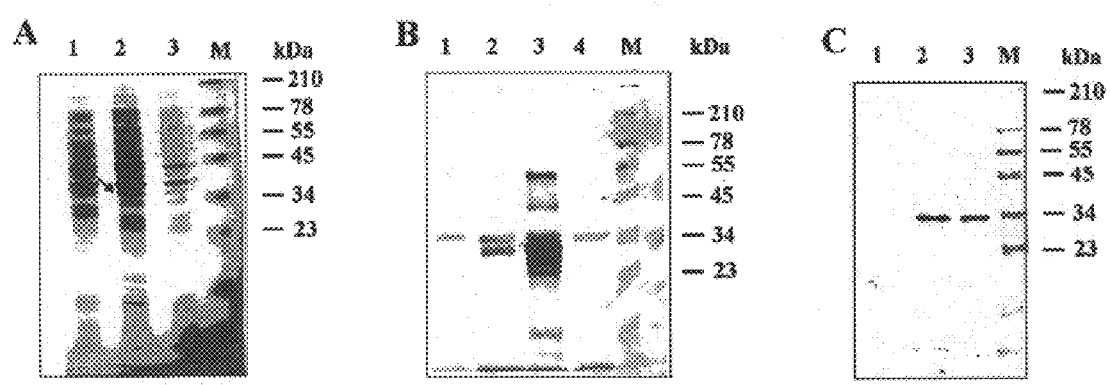
FIGS. 5 A–C are photographs showing the expression and processing of IBDV proteins in BL21 *E. coli* cells.

To show viral protein expression and processing, BL21 cells carrying the pKBVI206 plasmids were treated with 1mM IPTG for 14 hours. at room temperature and the cell extract were subjected to SDS polyacrylamide gel electrophoresis. From the coomassie blue staining one could detect a bend of 32 kDa similar in size to the mature IBDV VP3 (FIG. 5A, lane 2). This band does not appear in the control BL21 cells carrying pET21a and in uninduced BL21-pKVI206 (FIG. 5A, lanes, 1 and 3 respectively).

To show conclusively that the newly expressed protein is IBDV protein, Western analysis using anti-IBDV serum from infected chicken were performed. Induction of 45, 32 and 28 kDa proteins from BL21-pKVI206 cells reacted positively with anti-IBDV antiserum (FIG. 5B lane 3). Similar 32 kDa VP3 from infected bursa that was used as positive control could be detected (FIG. 5B lane 2 containing IPTG induced pKVI206-BL21 cells). Samples from extracts of the negative control did not react with the antiserum (FIG. 5B lanes 1 and 4; uninfected bursa tissue and IPTG induced pET21a-BL21 cells respectively). The presence of the mature viral proteins in the induced BL21-pKVI206 cells is an indication that the large IBDV polyprotein was processed into mature proteins as was expected.

Figure 6:
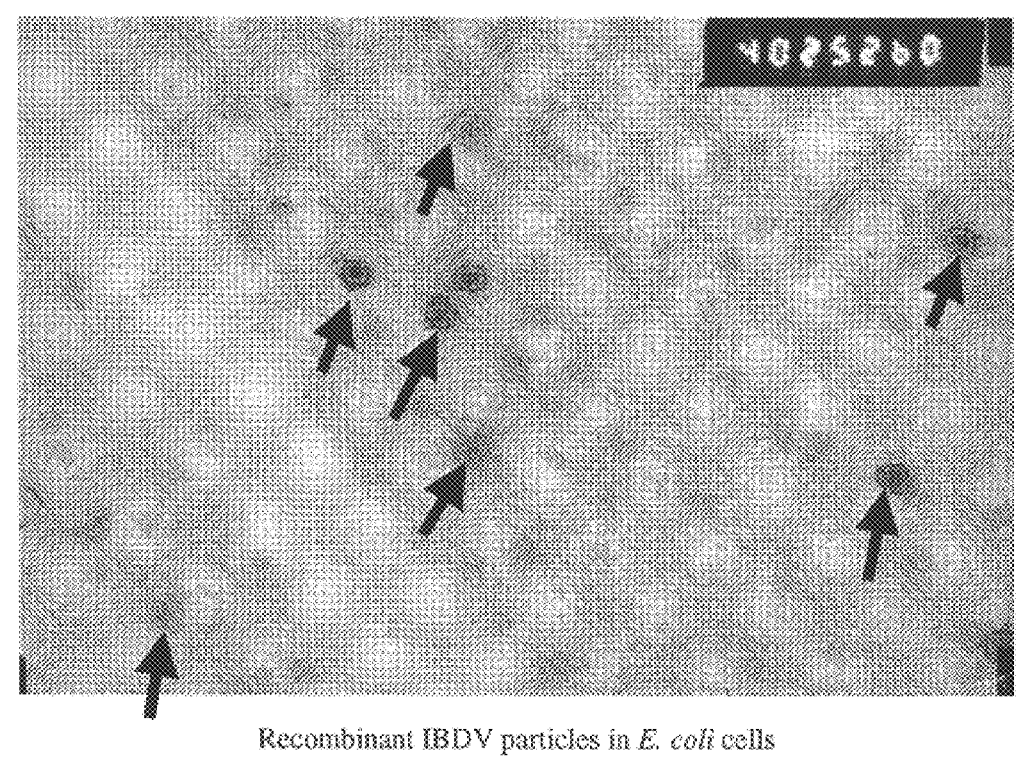

Immuno-electronmicroscopy analysis revealed virion like structures in the induced cells following expression. Electron microscopy grids covered with anti-IBbV serum were used to capture viral proteins and the same serum was used to decorate the captured virions. In extracts taken from induced BL21 pKVI206, virion structures were present which appeared to be similar to those virion structures found in IBDV infected bursal cells (FIG. 6).

For testing the immunogenicity, recombinant empty virions were purified using Affi gel Hz (BioRad) affinity chromatography. Chicken anti-IBDV antibodies were coupled to the matrix and induced *E. coli* and IBDV infected bursa extracts were used to purify the viral proteins. It was demonstrated that IBDV proteins were purified as can be, seen by the presence of the 32 kDa VP3 in a coomassie blue stained poilyacrylamide gel (PAGE), Western analysis (FIG. 5C) and viral particles in immunoelectronmicroscopy (FIG. 6).

Results of Administration of Vaccine

To test recombinant viral empty particles immunogenicity, a vaccine constitute of purified viral particles oil adjuvant was used to vaccinate young chicks.

Groups of 10–12 chickens were injected with viral empty particles purified from BL21-pKVI206 cells, viral particles purified from infected bursa, New Gamburite (Shafit's commercial vaccine) and column purified extract from BL21-pET21a cells. The chickens were vaccinated again three weeks later as a booster and three weeks later the chickens were challenged with a virulent IBDV virus isolated from the bursa of young infected chickens. Before challenge samples were analyzed by monitoring the induction of anti-IBDV antibodies.

Figure 7:
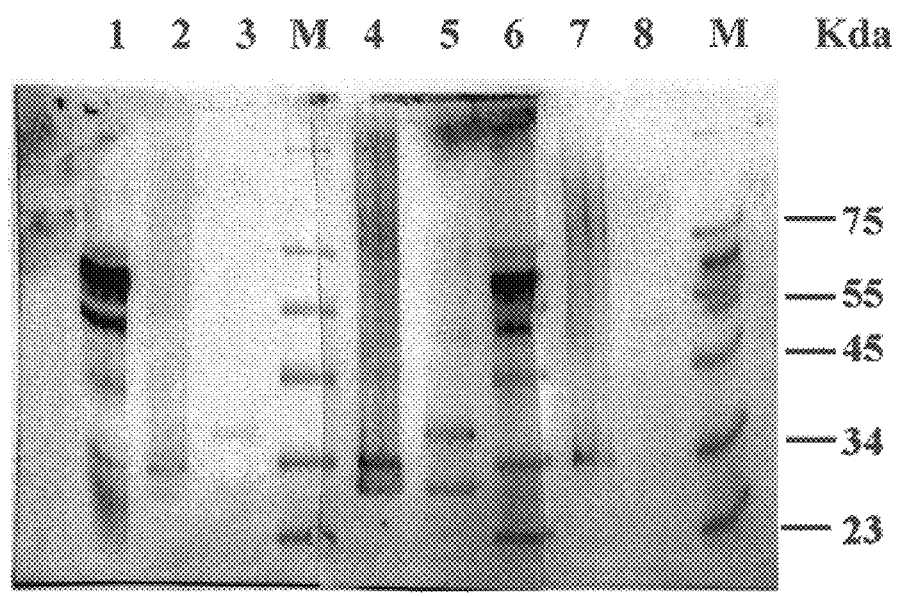
FIG. 7 is a photograph showing the Western blot analysis of anti-IBDV antibodies in the serum of chickens vaccinated with purified recombinant empty particles.
Figure 10:
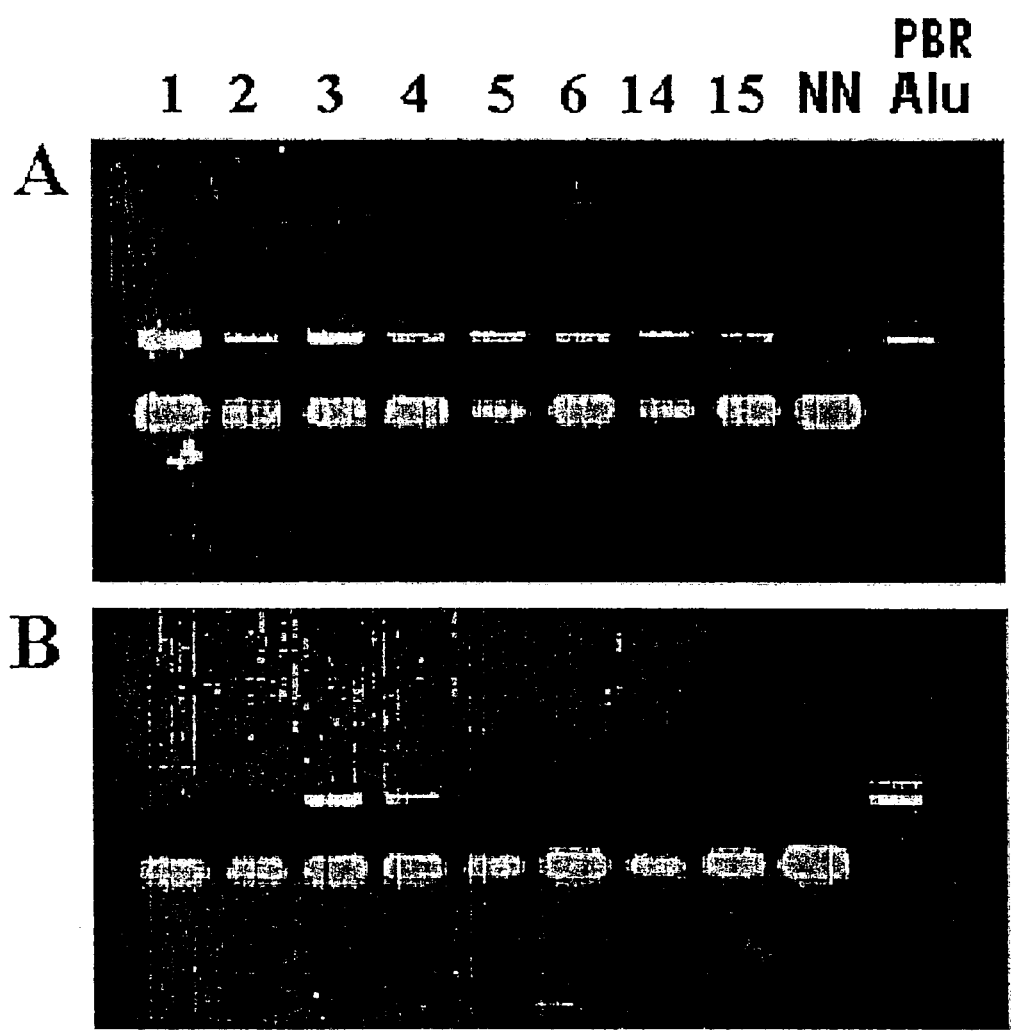
FIGS. 10 A and B are photographs showing the RT-PCR of an IBDV internal sequence in transgenic potato plants indicating the expression of IBDV RNA in the tubers, the arrow indicated the amplified PCR product.

In 75% of the tested chickens vaccinated with recombinant empty particles, antibodies could be detected as tested by Western analysis (FIG. 7). Testing included a Western blot analysis of anti-IBDV antibodies in the serum of vaccinated chicken with purified recombinant empty IBDV particles. The proteins from the pKVI206-BL21 cells were electrophoresed on SDS-PAGE and subsequently blotted onto a nitrocellulose sheet. The lanes on the blot were separated and each was reacted with the serum of a different chicken as the source of primary antibodies (lanes 14). When challenged, 10 out of 11 chickens of the group, which were immunized with the recombinant vaccine, survived and did not show any disease symptoms (Table 1). Moreover, viral antigen was not detected in all of the chickens in the group, indicating the inability of the challenged virus to replicate in the chickens vaccinated with the recombinant vaccine. The cause of death of the one chicken that died in the immunized. group was not related to IBDV infection since viral antigens could not be detect in the serum of the dead chicken (Table 1).

Nine out of 11 chickens vaccinated with extracts from BL21-pET21a cells and 4 out of 10 of the control, non vaccinated chickens, died after challenged. Viral antigen were found in all chickens of the two groups indicating virus replication. In the positive control group in which the chickens were vaccinated with "Shafit" commercial vaccine none of the chickens showed any disease symptoms and no virus antigen was found (Table 1).

EXAMPLE 2

Expression of IBDV Particles in Potato (*Solanum Tuberosum*) and Tobacco Plants (Nicotiana Tabacum) Plants Materials Methods and Results Plasmid Construction The plasmid pBIN m-gfp5-ER, carrying a modified GFP gene, was obtained from Dr Jim Haseloff, Haseloff J, (1997). The polylinker of pBluescipt KS and the GUS gene were introduced in place of GFP, and the plasmid was named p103.

The GUS gene was pulled out of p103 by digesting with Xbal and Sacd. The sticky ends of the vector were made blunt with T4-DNA polymerase and re-ligated. This plasmid was named p203. An EcoRI fragment (IBDV genes VP2, VP3 3.2 Kb) was cloned from the bursa of infected chickens by RT-PCR . The gene was inserted into the binary vector p203 at the EcoRi site, downstream from the 35S constitutive (CaMV ) promoter (FIG. 9).

The engineered binary vector was named p203-IBDV. The orientation of the IBDV genes in the engineered binary plasmid was examined by PCR, colony hybridization and sequencing.

The plasmid p203-IBDV was introduced into the *Agrobactedum tumefaciens* strain LBA4404 by electroporation (Bio-Rad Gene Pulser II apparatus, cuvette gap 0.2 cm, voltage 2.5 kV Capacitor 25 $\mu$F. Resistor 200Ω Time Constant 4–5 msec). The electroporated bacteria were subsequently selected. by PCR and by selection with the antibiotic rifampicin.

Plant Transformation

Leaf disks of tobacco plants (*Nicotiana tabacum* cv.SR1 or NN) or mini tuber disks from potatoes (*Solanum tuberosum* cv. Desiree) were transformed according to the technique detailed in Horsch et al (1985) for tobacco plants and as described by Snyder and Belknap (1993), with the transfected A. *tumefaciens* harboring p203-IBDV and incubated on a regeneration medium composed of MS salt and vitamin mixture (M0222 Duchefa) supplemented with 2% sucrose, 1% mannitol, 2 mg/l zeatin, 0.1 mg/l indoleacetic acid, 300 mg/l kanamycin (Km). and 1% Noble agar (pH 5.8). Regenerating shoots were transferred individually to a medium containing MS salt and vitamin mixture, 3% sucrose, 300 mg/l of Km and 1% Noble agar (pH 5.8).

Transgenic rooted plantlets were transferred to soil and grown in a greenhouse at 25° C. under a 16 hours light 8 hours dark daily cycle. These plants were also self-pollinated and their seeds were collected and germinated on Km-containing MS medium to have R1 generation.

DNA Extraction and PCR Reaction

Twenty two independent adult transgenic plants were used for PCR. DNA was extracted from fresh tissue, as described by Edwards, et al, (1991).

The PCR reaction mixture (25 $\mu$l) consisted of 25 mM Tris HCI, pH 9.3, 50 mM KCI, 2 $\mu$l MgCI2, 1 mM β-mercapthoethanol, 50 $\mu$M of each of the four dNTPs, 150 ng of each primer: Primers for VP2: sense #93, and antisense #92.(Stram et al 1994). DNA template 150–300 ng, 2.5 units of Taq DNA polymerase (Advanced Biotechnology). The reaction mixture was subjected to initial denaturation of the genomic DNA at 94° C. for 10 minutes, followed by 1 minute at 56° C. The reaction mixture was then incubated for 2 minutes at 72° C. and further subjected to 40 PCR cycles ( each consisting of 30 seconds at 92° C., 30 seconds at 55° C., and 30° C. seconds at 72° C.), concluding with a 7 minutes incubation at 72° C. RT-PCR Total RNA was extracted from transgenic plants leaves (for Tobacco) and tubers for potatoes (Tri reagent, Sigma). RNA (2 $\mu$g) was taken for reverse transcription (RT) reaction in a final volume of 20 $\mu$l using AMV reverse transcriptase (Promega) according to the manufacturer's instructions. The reaction was carried out at 42° C. for 1 hour. All the RT reaction mixture served as a template for a PCR, carried out at 94° C. for 10 minutes followed by 30 cycles of 94° C. (30 seconds); 58° C. (30 seconds); 72° C. (30 seconds). The sequences of the IBDV PCR primers are as described by Stram et al. (1994). or of a NOS terminator (this primer is located on the part of Nos- terminator beyond the poly A site. Therefore it will be found on the DNA but not on the transcribed RNA). The reaction products were separated on a 1.5% agarose gel.

The reaction products are shown in FIGS. 10 A and B, with the arrow indicating the amplifies PCR product. Specifically, FIG. 10A depicts in Lane 1 the positive control which is the PCR using the binary plasmids pBi203 as a template. Lanes 2–6 and 14–15 show the PCR results using transgenic potato tuber DNA from the respective lines as a template. Lane NN, the negative control depicts the PCR product using non-transgenic potato tuber DNA as a template. Lane PBR Alu shows the DNA of molecular size markers. Regarding FIG. 10B, Lane 1 is the negative control which shows the PCR product using the binary plasmids pBi203 as a template. Lanes 2–6 and 14–15 show the RT-PCR results using transgenic potato tuber RNA from the respective lines as a template. Lane NN, the negative control depicts the RT-PCR product using non-transgenic potato tuber RNA from line 3 as a template, however the RT enzyme was omitted from the reaction mixture.

Western Blotting

Protein was extracted in the following extraction buffer (2 ml/gr fresh tissue) Edelbaum et al, (1990). 20 mM Tris-HCI, pH 7.5, 150 mM KCI, 7 mM Mg acetate, 150 mM glucose, 30 mM 2-mercaptoethanol, 1 mM EDTA, 1 mM benzamidine, 100 $\mu$M phenylmethylsulfonyl fluoride, 10% (v/v) glycerol and 0.5%(v/v) NP-40. The homogenate was centrifuged at 15,000 g, 4° C. for 15 minutes and the supernatant fluid was aliquoted and kept at –80° C. Protein content was determined according to Bradford (1976). Proteins were electrophoresed in 12.5% SDS-polyacrylamide gels according to Laemmli (1970), and. electroblotted onto nitrocellulose membranes was according to Towbin et al. (1979). The membrane was incubated with Rabbit anti IBDV antiserum at a 1:100 or 1:500 dilution for 16 hours at 4° C. This was followed by a 60-minute incubation with $10^6$ dpm of $^{125}$I-labeled Protein A (IM144, Amersham). Following washing, the membrane was subjected to phosphoimaging (Fuji imaging plate) followed by autoradiography. The autoradiograph was scanned by the Power Look 200 apparatus (Umax) and subjected to an integrated band-intensity-area data analysis (NIH.Image 1.61) (FIG. 8). The lanes showed the following results: lane 1 showed the molecular weight marker; Lane C1–3 show the controls of proteins from non-transgenic potatoes; lanes 7-1-7-3 and B1 show the proteins from infected bursa; and lane B2 shows the proteins from infected bursa diluted 1:10.

The Transgenic Plants

All the transgenic tobacco and potato plants are of Ro generation. They all have flowered and set seeds.

Throughout this application, various publications, are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

TABLE 1

| Vaccine | Bursa AGP | Av. Weight (gr) | Death following exposure |
|---|---|---|---|
| Gumborit ® 422019 (18-2-99) | − | 3.49 | 0/10 |
| Non vaccinated control | + | 1.24 | 5/12 |
| 2 × LB (14-1-99) & (2-2-99) | − | 1.24 | 1/11 |

REFERENCES

15th Chapter of Genetic Engineering of Plants.

Ausubel et al., Current Protocols in Molecular Biology, John Wiley and Sons, Baltimore, Maryland (1989).

Borrebaeck, *Antibody Engineering—A Practical Guide*, W. H. Freeman and Co., 1992.

Bradford, M. M, (1976). A rapid and sensitive method for the quantitation of microgram quantities of protein utilizing the principle of protein dye binding. *Anal. Biochem.* 72: 248–254.

Edelbaum O., IIan N, Grafi G, Sher N, Stram Y, Novick D, Tal N, Sela I, Rubinstein M, (1990). Two antiviral proteins from tobacco: Purification and characterization by monoclonal antibodies to human β- interferon. *Proc Natl Acad Sci USA* 87: 588–592.

Edwards-K, Johnstone-C., Thompson-C. (1991). A simple and rapid method for the preparation of plant genomic DNA for PCR analysis. *Nucleic- Acids-Research.* 19: 6, 1349; 3 ref. Plant Biotechnology Section, ICI Seeds, Jealott's Hill Research Station, Bracknell, Berkshire, UK.

Harlow and Lane, *Antibodies: A Laboratory Manual*, Cold Spring Harbor Laboratory, Cold Spring Harbor, N.Y., 1988.

Haseloff J, Siemering K R, Prasher DC., Hodge S. (1997). Removal of a cryptic intron and subcellular localization of green fluorescent protein are required to mark transgenic Arabidopsis plants brightly. *Proc. Natl. Acad. Sci. USA.* 94: 2122–2127.

Horsch R B, Fry J E, Hoffman NL, Eichholtz D, Roger S G, Ffaley. (1985). RT: A simple and general method for transferring genes into plants. Science: 227: 1229–1231.

Huston et al, 1991 "Protein engineering of single-chain Fv analogs and fusion proteins" in Methods in Enzymology (J J Langone, ed.; Academic Press, New York, N.Y.) 203:46–88.

Johnson and Bird, 1991 "Construction of single-chain Fvb derivatives of monoclonal antibodies and their production in *Escherichia coli* in Methods in Enzymology (J J Langone, ed.; Academic Press, New York, NY) 203:88–99.

Johnstone & Thorpe, *Immunochemistry in Practice*, Blackwell Scientific Publications, Oxford, 1982.

Laemmli U. K, (1970). Cleavage of structural proteins during the assembly of the head of bacteriophage T4. Nature (London): 227: 680–685.

McCormac A C., Wu H, Bao M, Wang Y, Xu R, Elliott MC., Chen D-F. (1998). The use of visual marker genes as cell-specific reporters of Agrobacterum-mediated T-DNA delivery to wheat (*Tfiticum aestivum* L.) and barley (*Hordeum vulgare* L.) Euphytica 99:17–25.

Mernaugh and Mernaugh, 1995 "An overview of phage-displayed recombinant antibodies" in Molecular Methods In Plant Pathology (RP Singh and US Singh, eds.; CRC. Press Inc., Boca Raton, Fla.) pp. 359–365.

Mestecky et al, "Mucosal immunity and strategies for novel microbial vaccines" *Acto Paediatr Jpn*, 36(5):53744, 1994.

Mishell and Shiigi (eds), *Selected Methods in Cellular Immunology*, W. H. Freeman and Co., New York (1980).

*PCR Protocols: A Guide To Methods And Applications*, Academic Press, San Diego, Calif. (1990).

Salinovich, O. and Montelaro, R. C. (1986). Reversible staining and peptide mapping of proteins transferred to nitrocellulose after separation by sodium dodecyl sulfate-polyacrylamide gel electrophoresis. *anal. Biochem.* 156: 341–347.

Sambrook et al., *Molecular Cloning: A Laboratory Manual*, Cold Springs Harbor Laboratory, New York (1989, 1992).

Shalaby, "Development of oral vaccines to stimulate mucosal and systemic immunity: barriers and novel strategies" *Clin Immunol Immunopathol* 74(2):127–134, 1995.

Snyder G. W. and W. R. Belknap. (1993). A modified method for routine Agrobacterium mediated transformation of in vitro grown potato microtubers. Plant Cell Reports12: 324–327.

Stites et al. (eds), *Basic and Clinical Immunology* (8th Edition), Appleton & Lange, Norwalk, Conn. (1994).

Stram,Y,. Meir, T,. Molad, R, Blumenkranz, M, Malkinson, and Weisman. (1994). Applications of the polymerase chain reaction to detect infection Bursal Disease Virus in Naturally infected chickens. *Avian diseases* 38: 879–30 884.

Strober and James, "The Mucosal Immune System" *In Basic & Clinical Immunoloay* 8th Edition eds Stites, Te,rr, Parslow, (Appleton & Lange, 1994), pgs 541–551.

Testoni et al., 1996, Blood 87:3822.

Towbin H, Staehelin T. Gordon J. (1979). Electrophoretic transfer of proteins from polyacrylamide gels to nitrocellulose sheets: procedure and some applications. *Proc. NatlAcad. Sci. USA* 76: 4350–4354.

U.S. Pat. Nos. 3,791,932; 3,839,153; 3,850,578; 3,850,752; 3,853,987; 3,867,517; 3,879,262; 3,901,654; 3,935,074; 3,984,533; 3,996,345; 4,034,074; 4,098,876; 4,666,828; 4,683,202; 4,801,531; 4,879,219; 5,011,771; 5,192,659; 5,272,057, 5,281,521; 5,417,986; and 5,518,725.

What is claimed is:

1. A method of producing immunogenic IBDV particles, comprising expressing a sequence encoding IBDV VP2, VP3, and VP4 in transgenic plant cells.

2. The method of claim 1, further comprising extracting or purifying the particles from the transgenic plant cells.

3. The method of claim 1, wherein the particles are produced in transgenic plants.

4. The method of claim 3, wherein the plants are potato or tobacco plants.

5. A transgenic plant cell comprising a sequence encoding IBDV VP2, VP3, and VP4, which produces immunogenic IBDV particles.

6. A transgenic plant comprising a sequence encoding IBDV VP2, VP3, and VP4, which produces immunogenic IBDV particles.

7. The transgenic plant according to claim 6, which is a tobacco or potato plant.

8. A method for immunization of animals against IBDV, comprising oral administration of an effective immunizing amount of transgenic plant material comprising immunogenic IBDV particles made by expression of a sequence encoding IBDV VP2, VP3, and VP4 in transgenic plant cells.

9. The method of claim 8, wherein transgenic plant cells are administered.

10. An immunogenic composition comprising an effective immunizing amount of transgenic plant material comprising immunogenic IBDV particles made by expression of a sequence encoding IBDV VP2, VP3 and VP4 in transgenic plant cells.

11. The composition of claim 10, which comprises the transgenic plant cells.

* * * * *

SEQUENCE LISTING

<160> NUMBER OF SEQ ID NOS: 1

<210> SEQ ID NO 1
<211> LENGTH: 3054
<212> TYPE: DNA
<213> ORGANISM: Infectious bursal disease virus

<400> SEQUENCE: 1

| | | | | | |
|---|---|---|---|---|---|
| caaacgatcg | cacatatgac | aaacctgcaa | gatcaaaccc | aacagattgt | tccgttcata | 60 |
| cggagccttc | tgatgccaac | aaccggaccg | gcgtccattc | cggacgacac | cctagagaag | 120 |
| cacactctca | ggtcagagac | ctcgacctac | aatttgactg | tgggggacac | agggtcaggg | 180 |
| ctaattgtct | ttttccctgg | tttctctggc | tcaattgtgg | gtgctcacta | cacactgcag | 240 |
| agcaatggga | actacaagtt | cgatcagatg | ctcctgactg | cccagaacct | accggccagc | 300 |
| tacaactact | gcaggatagt | gagtcggagt | ctcacagtga | ggtcaagcac | actccctggc | 360 |
| ggcgtttatg | cactaaatgg | caccataaac | gccgtgttcc | aaggaagcct | gagtgaactg | 420 |
| acagatgtta | gctacaatgg | gttgatgtct | gcaacagcca | acatcaacga | caaaatcggg | 480 |
| aacgtcctag | taggggaagg | ggtaaccgtc | ctcagcttac | ccacatcata | tgatcttggg | 540 |
| tatgtgagac | tcggtgaccc | cattcccgct | atagggctcg | acccaaaaat | ggtagcaaca | 600 |
| tgtgacagca | gtgacaggcc | cagagtctac | accataactg | cagccgatga | ttaccaattc | 660 |
| tcatcacagt | accaagcagg | tggagtaaca | atcacactgt | tctcagctaa | tatcgatgcc | 720 |
| atcacaagcc | tcagcatcgg | ggaagaactc | gtgtttcaaa | caagcgtcca | aggccttata | 780 |
| ctgggcgcta | ccatctacct | tataggcttt | gatgggactg | cggtaatcac | cagagctgtg | 840 |
| gccgcagaca | atgggctaac | ggccggcact | gacaacctta | tgccattcaa | tattgagatt | 900 |
| ccaaccagcg | agataaccca | gccaatcaca | tccatcaaac | tggagatagt | gacctccaaa | 960 |
| agtggtggcc | aggcggggga | tcagatgtca | tggtcagcaa | gtgggagcct | agcagtgacg | 1020 |
| atccacggtg | gcaactatcc | aggggccctc | cgtcccgtca | cactagtagc | ctacgaaaga | 1080 |
| gtggcaacag | gatctgtcgt | tacggtcgcc | ggggtgagca | acttcgagct | gatcccaaat | 1140 |
| cctgaactag | caaagaacct | ggtcacagaa | tacggccgat | tgacccagg | ggccatgaac | 1200 |
| tacacaaaat | tgatactgag | tgagagggac | cgtcttggca | tcaagaccgt | gtggccaaca | 1260 |
| agggagtaca | ctgactttcg | cgagtacttc | atggaggtgg | ccgacctcaa | ctctcccctg | 1320 |
| aagattgcag | gagcatttgg | cttcaaagac | ataatccggg | ccctaaggag | gatagctgtg | 1380 |
| ccggtggtct | ctacactgct | cccacccgcc | gctccctag | cccatgcaat | tggggaaggt | 1440 |
| gtagactacc | tgctgggcga | tgaggcacaa | gctgcttcag | gaactgctcg | agccgcgtca | 1500 |
| ggaaaagcaa | gagctgcctc | aggccgcata | aggcagctaa | ctctcgccgc | cgacaagggg | 1560 |
| tacgaggtag | tcgcgaatct | gtttcaggtg | ccccagaatc | ctgtagtcga | cgggattctc | 1620 |
| gcttcacctg | gggtactccg | cggtgcacac | aacctcgact | gcgtgttgag | agagggtgcc | 1680 |
| acgctatttc | ctgtggtcat | cacgacagtg | gaagatgcca | tgacacccaa | agcgctgaac | 1740 |
| agcaaaatgt | ttgctgtcat | tgaaggcgtg | cgagaagatc | tccaacctcc | atctcaaaga | 1800 |
| ggatccttca | tacgaactct | ctccggacat | agagtctatg | gatatgctcc | agatgggta | 1860 |
| cttccactgg | agactgggag | agattacacc | gtggtcccaa | tagatgatgt | ctgggacgac | 1920 |
| agcattatgc | tgtccaatga | ccccatacct | cctattgtgg | gaaacagcgg | aaacctagcc | 1980 |
| atagcttaca | tggatgtgtt | tcgacccaaa | gtccccatcc | atgtggccat | gacgggagcc | 2040 |

-continued

```
ctcaacgcct atggcgagat tgagaacgtg agctttagaa gcaccaagct cgccactgca    2100
caccgacttg gcctcaagtt ggctggtccc ggtgcatttg acgtgaacac cgggtccaac    2160
tgggcgacgt ttatcaaacg ttttcctcac aatccacgcg actgggacag gctcccttac    2220
ctcaaccttc cataccttcc acccaatgca ggacgccagt acgacctggc catggccgct    2280
tcagagttca aagagacccc cgaactcgag agcgccgtca gagccatgga agcagcagcc    2340
aacgtggacc cactgttcca atctgcgctc agcgtgttca tgcggctgga agagaatggg    2400
attgtgactg atatggccaa cttcgcactc agcgacccga acgcccatcg gatgcgcaat    2460
tttctcgcaa acgcaccaca agcaggcagc aagtcgcaaa gagccaagta cgggacagca    2520
ggctacggat tggaagcccg gggccccact ccagaggaag cacagaggaa aaaagacaca    2580
cggatatcaa agaagatgga gactgtgggc atctactttg caacaccaga atgggtagca    2640
ctcaatgggc accgggggcc aagccccggc cagctaaagt actggcagaa cacacgagaa    2700
atacctgatc caaacgagga ctacctagac tacgtgcatg cagagaagag ccggttggca    2760
tcagaagaac aaatcctaag ggcagctacg tcgatctacg gggctccagg acaggcagag    2820 ccacccagg ccgtcataga cgaagtcgcc aaagtctatg aaatcaacca tgggcgtggc    2880
cccaaccaag aacagatgaa agatctgctc ttgactgcga tggagatgaa gcatcgcaat    2940
cccaggcggg ctccaccaaa gcccaagcca aaacccaatg ttccaacaca gagaccccct    3000
ggtcggctgg gccgctggat cagggctgtc tctgacgagg accttgagta aggc          3054
```